US010548573B2

(12) United States Patent
Lerch et al.

(10) Patent No.: US 10,548,573 B2
(45) Date of Patent: Feb. 4, 2020

(54) COMBINED ULTRASOUND-COMPUTED TOMOGRAPHY IMAGING

(71) Applicant: Siemens Healthcare GmbH, Erlangen (DE)

(72) Inventors: Daniel Lerch, Weilersbach (DE); Carsten Thierfelder, Pinzberg (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 379 days.

(21) Appl. No.: 15/440,274

(22) Filed: Feb. 23, 2017

(65) Prior Publication Data
US 2017/0258454 A1 Sep. 14, 2017

(30) Foreign Application Priority Data

Mar. 9, 2016 (DE) .................. 10 2016 203 812

(51) Int. Cl.
*A61B 8/08* (2006.01)
*A61B 6/03* (2006.01)
*A61B 6/00* (2006.01)
*A61B 8/00* (2006.01)

(52) U.S. Cl.
CPC ............ *A61B 8/5261* (2013.01); *A61B 6/032* (2013.01); *A61B 6/5247* (2013.01); *A61B 8/4444* (2013.01); *A61B 8/481* (2013.01); *A61B 8/5207* (2013.01); *A61B 8/5238* (2013.01); *A61B 8/54* (2013.01); *A61B 8/56* (2013.01)

(58) Field of Classification Search
CPC ..... A61B 8/5261; A61B 8/0891; A61B 6/541; A61B 6/4417; A61B 8/5207; A61B 6/5247; A61B 8/5238; A61B 8/481; A61B 8/56; A61B 8/54; A61B 6/032; A61B 8/4444
See application file for complete search history.

(56) References Cited

U.S. PATENT DOCUMENTS

2014/0005535 A1  1/2014 Edic
2015/0313578 A1  11/2015 Yu
2018/0235563 A1* 8/2018 Nam ..................... A61B 5/742

FOREIGN PATENT DOCUMENTS

EP          1504713 A1    2/2005

OTHER PUBLICATIONS

German Office Action dated Feb. 7, 2017.

* cited by examiner

*Primary Examiner* — Rex R Holmes
(74) *Attorney, Agent, or Firm* — Harness, Dickey & Pierce, P.L.C.

(57) ABSTRACT

A system includes a medical imaging apparatus embodied for the acquisition of first items of imaging data based on electromagnetic radiation, and a control apparatus embodied to control the medical imaging apparatus and to control an ultrasound probe. The control apparatus includes an interface embodied to output control commands to the ultrasound probe. The ultrasound probe can be connected to the control apparatus via the interface.

27 Claims, 5 Drawing Sheets

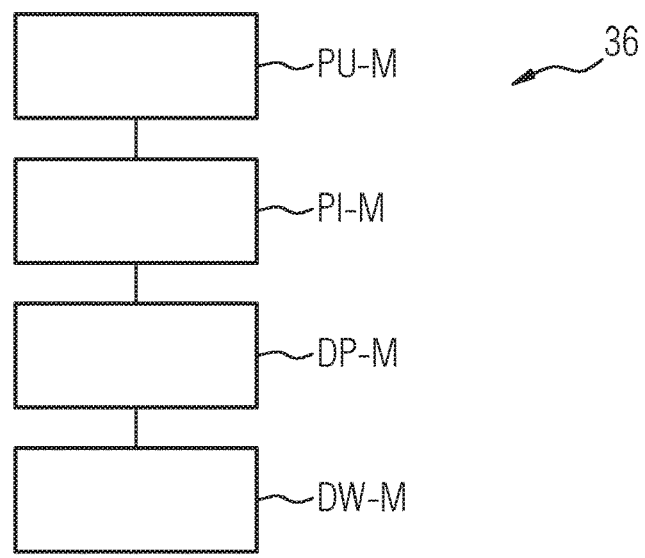
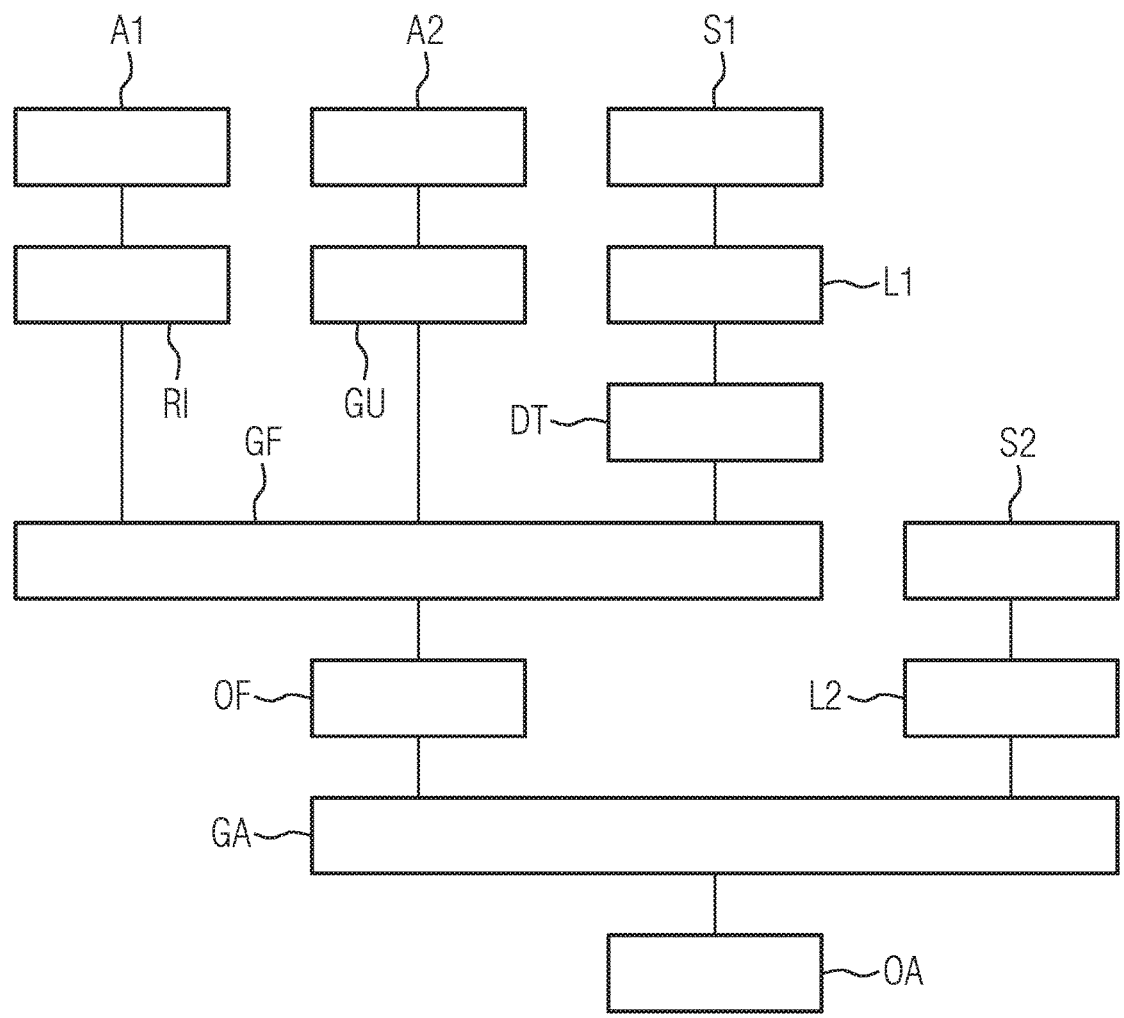

COMBINED ULTRASOUND-COMPUTED TOMOGRAPHY IMAGING

PRIORITY STATEMENT

The present application hereby claims priority under 35 U.S.C. § 119 to German patent application number DE 102016203812.5 filed Mar. 9, 2016, the entire contents of which are hereby incorporated herein by reference.

FIELD

At least one embodiment of the invention generally relates to a system with a medical imaging apparatus embodied for the acquisition of first items of imaging data based on electromagnetic radiation and a control apparatus embodied to control the medical imaging apparatus and to control an ultrasound probe.

At least one embodiment of the invention further generally relates to a method for setting an operating state of a medical imaging apparatus embodied for the acquisition of first items of imaging data based on electromagnetic radiation and to a method for the determination of a transformation for image registration of an ultrasound data set and a medical image data set recorded with electromagnetic radiation.

At least one embodiment of the invention further generally relates to a method for the determination of a flow parameter relating to a fluid flow in a segment of a vessel, a flow parameter determining facility and a system with a flow parameter determining facility.

BACKGROUND

A combination of ultrasound imaging and imaging based on electromagnetic radiation, for example computed tomography, is of interest for a variety of reasons. Hereinafter, the combination of ultrasound (US) and computed tomography (CT) will also be called US-CT. US-CT imaging makes it possible, for example, to improve interventions in that a CT volume image and an image recorded with an ultrasound biopsy probe are superimposed. This enables the desired region to be reached with a higher aiming precision. When ultrasound imaging is used in addition to CT, a stand-alone ultrasound device is frequently placed next to the computed tomography device. A configuration of this kind is not optimal for many applications with regard to the interaction of components of the ultrasound device and components of the computed tomography device.

SUMMARY

At least one embodiment of the invention enables improved interaction between a medical imaging apparatus embodied for the acquisition of first items of imaging data based on electromagnetic radiation and an ultrasound probe.

At least one embodiment of the invention is directed to a system; at least one embodiment of the invention is directed to a method; at least one embodiment of the invention is directed to another method; and at least one embodiment of the invention is directed to a synchronization facility. The claims address further advantageous embodiments of the invention.

The system according to at least one embodiment of the invention comprises a medical imaging apparatus embodied for the acquisition of first items of imaging data based on electromagnetic radiation and a control apparatus embodied to control the medical imaging apparatus and to control an ultrasound probe. The control apparatus comprises an interface embodied to output control commands for controlling the ultrasound probe to the ultrasound probe. The ultrasound probe can be connected to the control apparatus via the interface.

According to one embodiment of the invention, it is provided that the medical imaging apparatus comprises a gantry and/or a patient support apparatus and/or that the mobile control unit is arranged or can be arranged on the gantry and/or on the patient support apparatus. The mobile control unit, in particular the tablet computer, can be arranged or arrangeable in the vicinity of the patient support apparatus and/or in the vicinity of the gantry such that both the mobile control unit and the patient supported on the patient support apparatus and/or operating elements arranged on the gantry for operating the medical imaging apparatus are simultaneously within the user's reach. This enables the user to be shown images in the vicinity of the patient, wherein the user is simultaneously able to operate the medical imaging apparatus.

According to one embodiment of the invention, it is provided that the system comprises an injection apparatus embodied for the application of a contrast medium for the acquisition of the first items of imaging data based on electromagnetic radiation and/or for the application of an ultrasound contrast medium. In particular, the injection apparatus can be used to inject the patient with a contrast medium for the acquisition of the first items of imaging data based on electromagnetic radiation and/or an ultrasound contrast medium simultaneously and/or substantially simultaneously and/or at a specified time interval. The control apparatus can, for example, be embodied to control the injection apparatus.

In at least one embodiment, the method for setting an operating state of a medical imaging apparatus embodied for the acquisition of first items of imaging data based on electromagnetic radiation in dependence on a temporal course of a movement of an anatomical structure and/or in dependence on a spatial distribution of an ultrasound contrast medium in the anatomical structure, comprises the following steps:

provision of an ultrasound data set relating to a temporal course of a movement of the anatomical structure and/or a spatial distribution of an ultrasound contrast medium in the anatomical structure, determination of a trigger time based on the ultrasound data set, outputting a trigger command on the onset of the trigger time, wherein the trigger command effects the setting of the operating state of the medical imaging apparatus.

In at least one embodiment, the method for the determination of a transformation for image registration of an ultrasound data set and a medical image data set record recorded with electromagnetic radiation relative to one another comprises the following steps:

acquisition of first items of imaging data via a medical imaging apparatus based on electromagnetic radiation, acquisition of second items of imaging data via an ultrasound probe, acquisition of first items of locating data relating to the ultrasound probe via a locating system selected from the location system group consisting of a camera system, an optical sensor system, a light reflection system, a radio direction-finding system and combinations thereof, determination of a first piece of positional information relating to a position of the ultrasound probe relative to a reference system of the medical imaging apparatus based on the first items of locating data, reconstruction of the medical image data set based on the first items of imaging data, generation of the ultrasound data set based on the second items of imaging data, determination of the transformation for image registration of the ultrasound data set and the medical image data set relative to one another based on the first piece of positional information.

In at least one embodiment, the method for the determination of a flow parameter relating to a fluid flow in a segment of a vessel comprises the following steps:

provision of an ultrasound data set relating to a region to be depicted in which the vessel is located, provision of a medical image data set recorded on the basis of electromagnetic radiation and relating to the region to be depicted, determination of positional information with which the segment of the vessel can be localized in the ultrasound data set based on the medical image data set, determination of the flow parameter relating to the fluid flow in the segment of the vessel relates to based on the ultrasound data set and based on the positional information.

According to one embodiment of the invention, it is provided that the system is embodied to carry out a method according to one or more of the embodiments described in this application. The system is in particular embodied to carry out a given step when the system comprises a component embodied to carry out the given step.

One embodiment of the invention provides that the control apparatus is formed by a computer and/or that one or more components of the control apparatus are formed at least partially by a computer. The computer can, for example, comprise a memory facility and/or a processor system. The processor system can, for example, comprise a microprocessor and/or a plurality of interacting microprocessors. One embodiment of the invention provides that the control apparatus and/or one or more components of the control apparatus is or are implemented at least partially in the form of software on a processor system.

One embodiment of the invention provides that the control apparatus and/or one or more components of the control apparatus is or are implemented at least partially in the form of hardware. The hardware can, for example, be an FPGA system (Field-programmable gate array), an ASIC system (application-specific integrated circuit), a microcontroller system, a processor system and combinations thereof. The hardware can, for example, interact with software and/or be configured by way of software. One embodiment of the invention provides that the control apparatus and/or one or more components of the control apparatus is or are at least partially formed by a cloud via cloud computing. The cloud can in particular comprise a network of memory regions that are spatially separated from one another and processor systems that are spatially separated from one another. The control apparatus can comprise a first cloud interface for the data transfer from the cloud and/or to the cloud.

Data transfer between components of the control apparatus can, for example, in each case take place via a suitable data transfer interface. One embodiment of the invention provides that data transfer interfaces for transferring data to and/or from components of the control apparatus are implemented at least partially in the form of software and/or at least partially in the form of hardware. In particular, the interfaces can comprises means for accessing suitable memory regions in which data can be suitably buffered, retrieved and updated.

In particular with an extensively software-based implementation of the control apparatus, a computer can be embodied by way of software such that the computer can carry out the steps of a method according to at least one embodiment of the invention. Hence, the object is in each case achieved by the computer program according to at least one embodiment of the invention, the computer-readable medium according to at least one embodiment of the invention and the computer program product according to at least one embodiment of the invention.

The computer program according to at least one embodiment of the invention can be loaded into a memory facility of a computer. The computer program carries out the steps of a method according to at least one embodiment of the invention when the computer program is executed on the computer. A computer program according to at least one embodiment of the invention is stored on the computer-readable medium according to at least one embodiment of the invention. In particular, the computer-readable medium can be embodied to transport the computer program and/or to store the computer program.

According to one embodiment of the invention, the computer-readable medium is a memory stick, a hard disk or some other kind of a data medium that can, for example, be transportable or permanently installed. The computer program according to at least one embodiment of the invention product comprises a computer program according to the invention and/or a computer-readable medium according to at least one embodiment of the invention. In addition to the computer program and/or the computer-readable medium, the computer program product can include additional software components, for example documentation, and/or additional hardware components, for example a hardware key (dongle etc.) for using the software.

BRIEF DESCRIPTION OF THE DRAWINGS

The invention is described again in more detail below with reference to the attached figures and with reference to exemplary embodiments. The representation in the figures is schematic and greatly simplified and not necessarily true to scale. In the context of this application, a term provided with a reference character can be understood to be an exemplary embodiment of the similarly named term which has not been given a reference character. If different reference characters are used for a term, this can in particular relate to different exemplary embodiments for this term.

The figures show.

DETAILED DESCRIPTION OF THE EXAMPLE EMBODIMENTS

Figure 1:
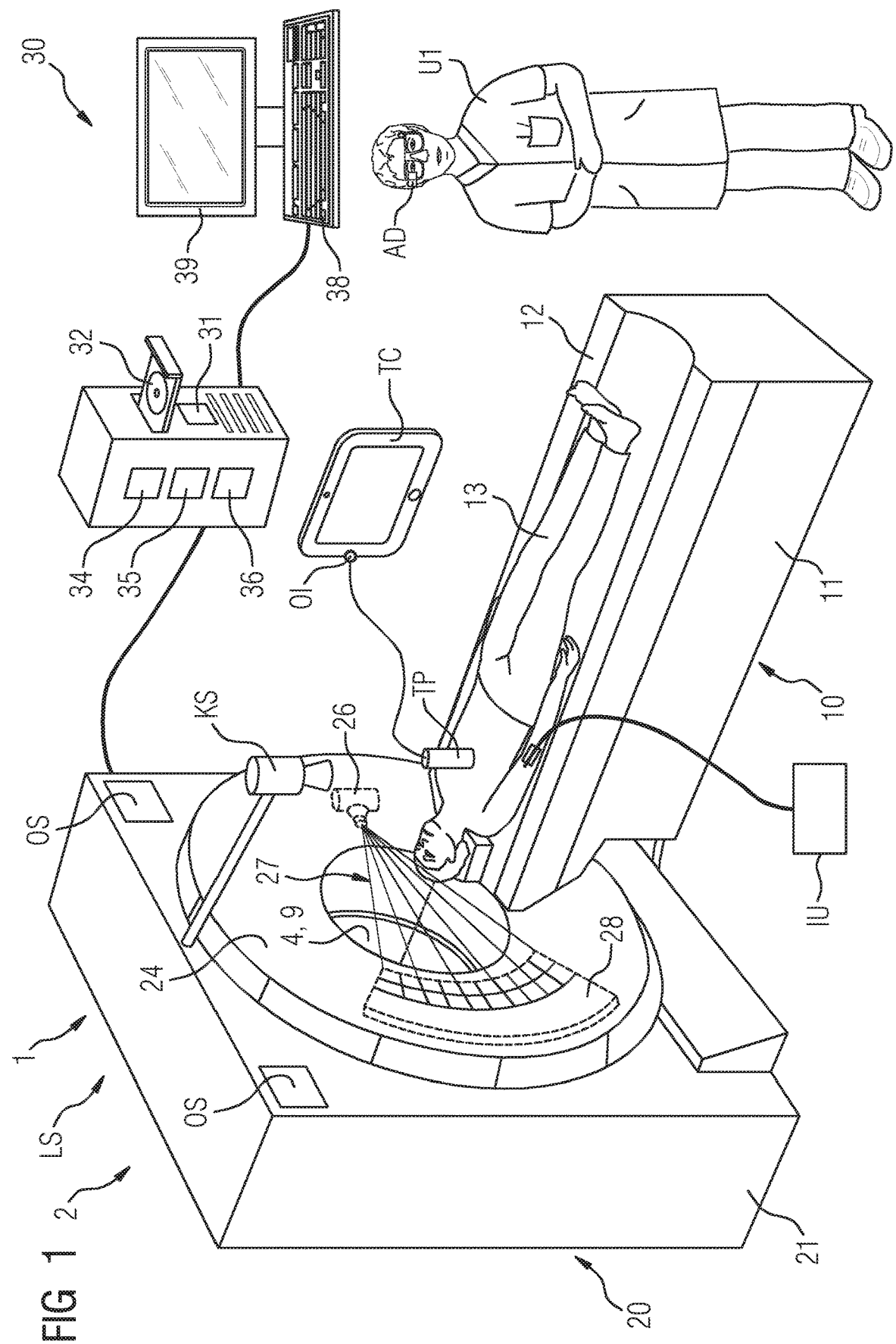
FIG. 1 a schematic representation of a system according to a first embodiment of the invention, FIG. 2 a schematic representation of a control apparatus, FIG. 3 a schematic representation of a synchronization facility according to a second embodiment of the invention, FIG. 4 a schematic representation of a flow parameter determining facility, FIG. 5 a flow diagram of a method for the determination of a transformation for image registration according to a third embodiment of the invention, FIG. 6 a flow diagram of a method for setting an operating state of the medical imaging apparatus according to a fourth embodiment of the invention, FIG. 7 a flow diagram of a method for the determination of a flow parameter relating to a fluid flow in a segment of a vessel, FIG. 8 a schematic representation of a vessel.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The system according to at least one embodiment of the invention comprises a medical imaging apparatus embodied for the acquisition of first items of imaging data based on electromagnetic radiation and a control apparatus embodied to control the medical imaging apparatus and to control an ultrasound probe. The control apparatus comprises an interface embodied to output control commands for controlling the ultrasound probe to the ultrasound probe. The ultrasound probe can be connected to the control apparatus via the interface.

The medical imaging apparatus can in particular be a non-ultrasound-based medical imaging apparatus. The medical imaging apparatus can, for example, be a tomography device and/or comprise a tomography device. The medical imaging apparatus can, for example, be embodied to reconstruct a medical image data set based on the first items of imaging data. Without restricting the general concept of the invention, in some of the embodiments of the invention described, the term computed tomography device can be used by way of example for the medical imaging apparatus.

According to one embodiment of the invention, the medical imaging apparatus is selected from the imaging modalities group consisting of an X-ray device, a C-arm X-ray device, a computed tomography device (CT device), a single photon emission computed tomography device (SPECT device), a positron emission tomography device (PET device), a magnetic resonance imaging device (MRI device) and combinations thereof. The medical imaging apparatus can further comprise a combination of an imaging modality selected, for example, from the imaging modalities group, and an irradiation modality. In this case, the irradiation modality can, for example, comprise an irradiation unit for therapeutic irradiation.

According to one embodiment of the invention, the medical imaging apparatus comprises an imaging data acquisition unit embodied for the acquisition of the first items of imaging data. In particular, the imaging data acquisition unit can comprise a radiation source and a radiation detector. One embodiment of the invention provides that the radiation source is embodied for the emission and/or excitation of radiation, in particular electromagnetic radiation and/or that the radiation detector is embodied to detect the radiation, in particular the electromagnetic radiation. The radiation can, for example, travel from the radiation source to a region to be depicted and/or, following interaction with the region to be depicted, travel to the radiation detector. On interaction with the region to be depicted, the radiation is modified and hence becomes a carrier of information relating to the region to be depicted. On the interaction of radiation with the detector, this information is acquired in the form of the first items of imaging data.

In particular in the case of a computed tomography device, the first items of imaging data can be projection data, the imaging data acquisition unit a projection data acquisition unit, the radiation source an X-ray source and the radiation detector an X-ray detector. The X-ray detector can in particular be a quantum-counting and/or energy-resolving X-ray detector. Without restricting the general concept of the invention, in some of the embodiments of the invention described, X-rays are named by way of example for the electromagnetic radiation. In particular in the case of a magnetic resonance imaging device, the first items of imaging data can be a magnetic resonance imaging data set, the imaging data acquisition unit a magnetic resonance imaging data acquisition unit, the radiation source a first radio-frequency antenna, the radiation detector the first radio-frequency antenna and/or a second radio-frequency antenna.

The ultrasound probe can, for example, be embodied to convert an electronic transmit signal into ultrasound, to output ultrasound, to receive ultrasound, to convert the ultrasound received into an electronic received signal, to convert the electronic received signal into second imaging data and/or to output the second items of imaging data. The electronic received signal can in particular be an analog electronic received signal. The second items of imaging data can in particular be digital second items of imaging data.

According to one embodiment of the invention, the ultrasound probe comprises a data transmission module embodied to receive the control commands from the interface and/or to output the second items of imaging data to the interface. The data transmission module can, for example, comprise a data transmission connection embodied for direct data transmission of the control commands from the interface and/or for direct data transmission of the second items of imaging data to the interface. The data transmission connector can, for example, be selected from the group consisting of a USB connector, a FireWire connector, a Bluetooth connector and combinations thereof. The direct data transmission can, for example, be cable-connected and/or wireless. Direct data transmission can in particular be understood to mean data transmission with which there are no data-processing steps, in particular no buffers and no amendments to the data transmission protocol, on the data transmission path between the interface and the data transmission connector.

According to one embodiment of the invention, the ultrasound probe comprises a beam former, an ultrasound converter array, receiver amplifiers and/or analog-to-digital converters. The beam former can, for example, comprise pulse generators, a memory element, a timer element, a time delay circuit, phase regulators and/or amplifiers. The ultrasound converter array can, for example, comprise a plurality of individual converters. The ultrasound converter array can, for example, comprise 64, 128 or 256 individual converters. The individual converters in the plurality of individual converters can, for example, each be based on the piezo effect and/or embodied to convert electrical energy into acoustic energy and/or to convert acoustic energy into electrical energy. The ultrasound converter array can, for example, be a phased array. In particular, the beam former and the ultrasound converter array can interact such that the outputting of ultrasound and/or the reception of ultrasound can both be achieved with a high degree of directionality.

The ultrasound probe can, for example, comprise a first housing and/or a second housing. The first housing can, for example, be dimensioned and/or shaped such that a user can hold the first housing with a first hand and guide it around a patient for the acquisition of second items of imaging data of a region to be depicted of the patient. The second housing can, for example, dimensioned and/or shaped such that the user can carry the second housing by way of a carrying apparatus, for example a carrying belt and/or hold it in a second hand while holding the first housing with the first hand and guiding it round the patient. According to one embodiment of the invention, the ultrasound converter array and/or the data transmission module is located in the first housing. According to one embodiment of the invention, all components of the ultrasound probe are located in the first housing. The beam former, the data transmission module, further components of the ultrasound probe and/or a battery to provide power to components of the ultrasound probe can each, for example, be located in the first housing and/or in the second housing. The first housing and the second housing can, for example, be connected to one another via a loom of cables for the transmission of electrical energy and/or electronic signals. The ultrasound probe can, for example, be an ultrasound biopsy probe.

According to one embodiment of the invention, the medical imaging apparatus comprises the control apparatus. The control apparatus is embodied to generate control commands to control the ultrasound probe and/or output the commands to the ultrasound probe via the interface. The connection of the ultrasound probe to the control apparatus via the interface can, for example, be cable-connected and/or wireless. The control commands can, for example, switch the output of ultrasound on and/or off and/or set one or more parameters of the ultrasound output and/or select a region of the patient to be examined via ultrasound. Parameters of the ultrasound output can, for example, be a power, a frequency, an alignment of an ultrasound bundle or the like.

In particular, the control commands can comprise control signals with which the beam former is controlled and/or pulse generators of the beam former are each individually controlled. The control commands can, for example, be used to set and/or adapt an operating mode of the ultrasound probe. The operating mode of the ultrasound probe can, for example, be selected from the operating mode group consisting of a B-mode operating mode, an M-mode operating mode, a 1D-operating mode, a 2D-operating mode, a 3D-operating mode, a 4D-operating mode, a Doppler operating mode, a color Doppler operating mode, a spectral Doppler operating mode, a contrast medium operating mode and combinations thereof.

At least one embodiment of the invention in particular enables the operation of an ultrasound probe by way of the control apparatus of a medical imaging apparatus embodied for the acquisition of first items of imaging data based on electromagnetic radiation. In particular, the hardware of the computers forming the control apparatus of the medical imaging apparatus can hence be used in a cost-saving manner to control the ultrasound probe. In addition, a patient support apparatus, positioning cushions, an input apparatus and an output apparatus of the medical imaging apparatus can be used in a cost-saving manner for ultrasound imaging by way of the ultrasound probe.

According to one embodiment of the invention, it is provided that the system comprises the ultrasound probe.

According to one embodiment of the invention, it is provided that the ultrasound probe is embodied for the acquisition of second items of imaging data. The second items of imaging data can, for example, relate to a region to be depicted, in particular a region to be depicted of a patient, wherein an anatomical structure is located in the region to be depicted. The second items of imaging data can, for example, comprise for each individual converter of the plurality of individual converters the individual converter imaging data assigned to the individual converter relating to the ultrasound received and/or converted by the individual converter.

According to one embodiment of the invention, it is provided that the interface is embodied to receive the second items of imaging data from the ultrasound probe.

According to one embodiment of the invention, it is provided that the control apparatus comprises an ultrasound data set generation module embodied for the generation of an ultrasound data set based on the second items of imaging data. The ultrasound data set can, for example, comprise spatially-resolved ultrasound image data and/or spatially-resolved ultrasound scan data. In particular, the ultrasound image data can relate to an image value, representing, for example, the intensity and/or the amplitude of ultrasound, which was reflected and/or transmitted in the region to be depicted. In particular, the ultrasound scan data can relate to a scan value acquired, for example via a Doppler method. A scan value of this kind can, for example, be a flow parameter relating to a fluid flow in a sub-region of a vessel. The ultrasound data set can, for example, comprise an ultrasound image with a plurality of image points, wherein each image point of the plurality of image points is assigned an image value and/or a scan value. The ultrasound data set can, for example, comprise an ultrasound image data set with a plurality of ultrasound images.

According to one embodiment of the invention, it is provided that the ultrasound probe is connected to the control apparatus via the interface.

According to one embodiment of the invention, it is provided that the interface is an open and/or universal interface. The interface can, for example, be a serial interface. In particular, the interface can be embodied to connect various peripheral devices to the control apparatus. The interface can be embodied in the form of both software, for example in the form of a data transmission protocol, and in the form of hardware, for example in the form of a plug-in connection and/or an antenna.

According to one embodiment of the invention, it is provided that the interface is selected from the interface group consisting of a Universal Serial Bus (USB) interface, a FireWire interface, a Bluetooth interface and combinations thereof.

According to one embodiment of the invention, it is provided that the control apparatus comprises a mobile control unit and/or that the mobile control unit comprises the interface.

The mobile control unit can, for example, comprise the ultrasound data set generation module. The mobile control unit can, for example, be connected to a stationary part of the control apparatus in a cable-connected or wireless manner. According to one embodiment of the invention, the mobile control unit is embodied to display a medical image data set reconstructed via the medical imaging apparatus based on the first items of imaging data and/or to display an ultrasound data set generated based on the second items of imaging data. According to one embodiment of the invention, the mobile control unit is embodied to generate control commands to control the ultrasound probe and/or to generate control commands to control the medical imaging apparatus. The control commands for controlling the medical imaging apparatus can, for example, be used to select a region to be depicted via the medical imaging apparatus of the patient and/or to start or finish the acquisition of first items of imaging data. The mobile control unit can, for example, comprise a touch-sensitive screen.

According to one embodiment of the invention, it is provided that the mobile control unit is a tablet computer.

According to one embodiment of the invention, software to control the ultrasound probe and/or to process the second items of imaging data and/or for the graphical display of the ultrasound data set is executed on the tablet computer.

According to one embodiment of the invention, it is provided that the medical imaging apparatus comprises a gantry and/or a patient support apparatus and/or that the mobile control unit is arranged or can be arranged on the gantry and/or on the patient support apparatus. The mobile control unit, in particular the tablet computer, can be arranged or arrangeable in the vicinity of the patient support apparatus and/or in the vicinity of the gantry such that both the mobile control unit and the patient supported on the patient support apparatus and/or operating elements arranged on the gantry for operating the medical imaging apparatus are simultaneously within the user's reach. This enables the user to be shown images in the vicinity of the patient, wherein the user is simultaneously able to operate the medical imaging apparatus.

According to one embodiment of the invention, it is provided that the system comprises an injection apparatus embodied for the application of a contrast medium for the acquisition of the first items of imaging data based on electromagnetic radiation and/or for the application of an ultrasound contrast medium. In particular, the injection apparatus can be used to inject the patient with a contrast medium for the acquisition of the first items of imaging data based on electromagnetic radiation and/or an ultrasound contrast medium simultaneously and/or substantially simultaneously and/or at a specified time interval. The control apparatus can, for example, be embodied to control the injection apparatus.

According to one embodiment of the invention, it is provided that the system comprises a location system selected from the location system group consisting of a camera system, an optical sensor system, a light reflection system, a radio direction-finding system and combinations thereof. The location system is embodied for the acquisition of first items of locating data relating to the ultrasound probe and/or for the acquisition of second items of locating data relating to a patient.

The location system can, for example, comprise a first subsystem for the acquisition of the first items of locating data and/or a second subsystem for the acquisition of the second items of locating data. The first subsystem and/or the second subsystem can, for example, be selected from the group consisting of a camera system, an optical sensor system, a light reflection system, a radio direction-finding system and combinations thereof. The optical sensor system can, for example, be embodied to scan the surface of the patient, wherein 2D-positional data and/or 3D-positional data can be generated from the surface of the patient. The first items of locating data can, for example, relate to a position, an alignment and/or a holding angle of the ultrasound probe.

The ultrasound probe can, for example, be acquired directly via the optical sensor system. Alternatively or additionally, infrared reflectors, which can be acquired via the optical sensor system, can be arranged on the ultrasound probe. The radio direction-finding system can, for example, be based on the triangulation of radio signals. The control apparatus can, for example, be embodied to control the location system.

According to one embodiment of the invention, the control apparatus further comprises the following components:
a first positional information determining module embodied to determine a first piece of positional information relating to a position of the ultrasound probe relative to a reference system of the medical imaging apparatus based on the first items of locating data,
a transformation determining module embodied for the determination of a transformation for image registration of an ultrasound data set and a medical image data set relative to one another based on the first piece of positional information. The image registration can, for example, be based on an elastic model.

According to one embodiment of the invention the control apparatus further comprises the following components:

a fusion image generating module embodied for the generation of a fusion image based on the ultrasound data set, the medical image and the transformation for image registration of the ultrasound data set and the medical image data set, a fusion image output module embodied to output the fusion image.

The fusion image can, for example, comprise the ultrasound image and the medical image, wherein the ultrasound image and the medical image are registered relative to one another by way of the transformation for image registration. The outputting of the fusion image can include a display of the fusion image, in particular via a display apparatus. Alternatively or additionally thereto, the outputting of the fusion image can include a data transmission of the fusion image and/or a storage of the fusion image in an image data memory facility, for example an image database.

The fusion image can, for example, be output via a screen in the form of a two-dimensional graphical display and/or via a virtual-reality apparatus as part of a virtual reality. The virtual reality can, for example, comprise the fusion image and/or further image elements, for example markings for positions of probes and/or needles.

According to one embodiment of the invention, the control apparatus further comprises the following components:

a second positional information determining module embodied to determine second positional information relating to a position of the patient relative to the reference system of the medical imaging apparatus based on the second items of locating data an augmented-reality information generating module embodied for the generation of augmented-reality information based on the fusion image and based on the second positional information, wherein augmented-reality information can be used to display the fusion image superimposed on the patient, an augmented-reality information output module embodied to output the augmented-reality information.

Augmented-reality information can in particular be understood to be information with which a reality, in particular the field of view of a user can be augmented. In particular, the augmented-reality information can be used to generate augmented reality on the basis of the field of view of the user. The augmented-reality information can in particular be output such that the field of view of the first user is augmented by the augmented-reality information. The outputting of the augmented-reality information can include the display of the augmented-reality information, in particular via an augmented-reality apparatus. Alternatively or additionally thereto, the outputting of the augmented-reality information can include data transmission of the augmented-reality information and/or storage of the augmented-reality information in an image data memory facility, for example an image database.

According to one embodiment of the invention, the system comprises an augmented-reality apparatus. The augmented-reality information can, for example, be generated and/or displayed via the augmented-reality apparatus. The term "device for generating augmented reality" and the term "augmented-reality apparatus" are used synonymously. The enhancement of reality is in particular known to the person skilled in the art by the term "augmentation". Enhanced reality is in particular known to the person skilled in the art in particular by the term "augmented reality". An enhanced-reality apparatus is in particular known to the person skilled in the art by the term "augmented-reality device".

According to one embodiment of the invention, the system comprises a third positional information determining module embodied to determine third positional information relating to a position of the augmented-reality apparatus relative to the reference system of the medical imaging apparatus.

One embodiment of the invention provides that a position and/or a direction of view of the user of the augmented-reality apparatus is determined and/or that a position and/or an alignment of the first augmented-reality apparatus is determined. The augmented-reality information can, for example, be generated based on the position and/or the direction of view of the user and/or based on the position and/or the alignment of the first augmented-reality apparatus. This can, for example, take place via the locating system and/or by way of movement information. The movement information can, for example, be acquired via one more acceleration sensors. In particular, the first augmented-reality apparatus can comprise one or more acceleration sensors.

In the case of more complex interventions (for example radio-frequency ablation, cryoablation or similar types of ablation of, for example, liver tumors and/or metastases) it is, for example, possible first to acquire a medical image data set, for example a CT volume image data set, from the target region via the medical imaging apparatus acquired. The location system, for example the optical sensor system, and/or spatial tracking of the ultrasound head of ultrasound probe during the acquisition of the second items of imaging data can be used to register the medical image data set relative to the patient in three-dimensional space. This enables the medical image data set together with the ultrasound data set to be displayed superimposed on the patient in real time in the form of augmented-reality information during an ultrasound-guided intervention.

In at least one embodiment, the method for setting an operating state of a medical imaging apparatus embodied for the acquisition of first items of imaging data based on electromagnetic radiation in dependence on a temporal course of a movement of an anatomical structure and/or in dependence on a spatial distribution of an ultrasound contrast medium in the anatomical structure, comprises the following steps:

provision of an ultrasound data set relating to a temporal course of a movement of the anatomical structure and/or a spatial distribution of an ultrasound contrast medium in the anatomical structure, determination of a trigger time based on the ultrasound data set, outputting a trigger command on the onset of the trigger time, wherein the trigger command effects the setting of the operating state of the medical imaging apparatus.

According to one embodiment of the invention, the following steps are provided:

acquisition of second items of imaging data of a region to be depicted in which the anatomical structure is located via an ultrasound probe, generation of the ultrasound data set based on the second items of imaging data.

According to one embodiment of the invention, the following step is provided:

acquisition of the first items of imaging data via the medical imaging apparatus based on the electromagnetic radiation.

The determination of the trigger time based on the ultrasound data set can include an automatic evaluation of the temporal course of the movement of the anatomical structure and/or the spatial distribution of the ultrasound contrast medium in the anatomical structure based on the ultrasound data set. Alternatively and/or additionally to the temporal course of the movement of the anatomical structure, the automatic evaluation can take account of a variable derived from the temporal course or a further course derived from the temporal course. This in particular includes a temporal derivation of the temporal course. The automatic evaluation can, for example, include the determination of a deviation of the temporal course, of the further course and/or the derived variable from one or more prespecified courses and/or variables. The spatial distribution of the ultrasound contrast medium in the anatomical structure can in particular include information on a temporal course of the spatial distribution of the ultrasound contrast medium in the anatomical structure. The dependence of a spatial distribution of an ultrasound contrast medium in the anatomical structure can in particular be or comprise a dependence of a temporal course of the spatial distribution of an ultrasound contrast medium in the anatomical structure. Alternatively and/or additionally to the spatial distribution of the ultrasound contrast medium in the anatomical structure, the automatic evaluation can take account of a variable derived from the spatial distribution or a further spatial distribution derived from the spatial distribution. This in particular includes a gradient of the spatial distribution and/or a temporal course of a gradient of the spatial distribution. The automatic evaluation can, for example, include the determination of a deviation of the spatial distribution, the further spatial distribution and/or the derived variable from one or more prespecified courses and/or variables.

The automatic evaluation can, for example, take place at prespecified, in particular regularly spaced, times. The trigger time can, for example, be the time at which the automatic evaluation reveals that the deviation determined falls below or exceeds a prespecified reference deviation. Alternatively, the trigger time can, for example, follow this time at a prespecified time distance.

The trigger command can, for example, be output in the form of a voltage and/or current pulse, a data packet or an instruction implemented in software and/or received by the control apparatus of the medical imaging apparatus. The control apparatus can in particular be embodied to set the operating state such that the operating state is set when the trigger command is received by the control apparatus. In this way, the trigger command can affect the setting of the operating state.

At least one embodiment of the described method for setting an operating state enables the operating state in particular to be set in temporal relationship to a movement of an anatomical structure and/or a temporal course of a distribution of a contrast medium due to blood flow. The setting of the operating state then in particular takes place in dependence on a temporal course of a movement of an anatomical structure and/or in dependence on a spatial distribution of an ultrasound contrast medium in the anatomical structure when the temporal course of a movement of an anatomical structure and/or the spatial distribution of the ultrasound contrast medium in the anatomical structure is used as the basis for the determination of a time the onset of which results in the setting of the operating state. Such a time can, for example, be the time of the trigger command, wherein the trigger command effects the setting of the operating state.

The operating state of the medical imaging apparatus can in particular be the acquisition operating state. The acquisition operating state can in particular be understood to be an operating state of the medical imaging apparatus in which the first items of imaging data are acquired. During the acquisition of the first items of imaging data, the electromagnetic radiation is typically generated via a radiation source such that the radiation can travel from the radiation source to a region to be depicted of a patient and, following interaction with the region to be depicted, travel to the radiation detector. The setting of the acquisition operating state in particular comprises the setting and/or changing of one or more parameters relating to the acquisition. Such parameters can, for example, be electronic and/or electromagnetic parameters. An electronic and/or electromagnetic parameter can in particular be understood to be a cathode current, an intensity of generated radiation or a power received and/or emitted by a radiation source.

With a combined computed tomography-ultrasound system, it would, for example, be conceivable, first to use the ultrasound component to measure the dynamics of the myocardium (heart muscle) relative to the heartbeat phase. The information can be used for the precise timing of the CT examination. This enables the time window of the application of the X-ray dose within the cardiac cycle to be optimized. This enables a higher hit accuracy to be ensured and/or the X-ray dose to be reduced.

Compared to conventional methods requiring a relatively expensive computed tomography device with high temporal resolution to produce high-quality coronary CT angiograms, the described method of at least one embodiment for setting the operating state enables the production of high-quality coronary CT angiograms with a less expensive computed tomography device with a lower temporal resolution. Alternatively, it is possible within certain limits, in the absence of a computed tomography device with high temporal resolution to obtain acceptable images by a more intensive use of the X-ray dose in that instead of (dose-saving) retrospective sequential recording methods, other (more dose-intensive) gating methods are used. By way of comparison, the invention enables the X-ray dose to be reduced.

For optimal acquisition of first items of imaging data, for example during vascular recording (arterial phase), it may be necessary to determine the time delay between the injection of a contrast medium and the acquisition. This can, for example, be performed prospectively via a test bolus and/or via bolus monitoring. In both cases, in addition to electromagnetic radiation, for example X-rays, and/or the contrast medium for the actual acquisition, further electromagnetic radiation and/or, in particular with a test bolus, also additional contrast medium is applied.

With a combined computed tomography-ultrasound system comprising an injection apparatus coupled to the control apparatus, the time delay between the injection and the arrival of the contrast medium in the vessels to be examined could be determined via the ultrasound probe and the ultrasound contrast medium without additional exposure to X-rays or an iodine contrast medium. The time delay can be used as the basis for determining the trigger time and outputting the trigger command. For a practiced ultrasound user, this would typically not require any more time than an examination via a test bolus.

In at least one embodiment, the method for the determination of a transformation for image registration of an ultrasound data set and a medical image data set record recorded with electromagnetic radiation relative to one another comprises the following steps:

acquisition of first items of imaging data via a medical imaging apparatus based on electromagnetic radiation,
acquisition of second items of imaging data via an ultrasound probe, acquisition of first items of locating data relating to the ultrasound probe via a locating system selected from the location system group consisting of a camera system, an optical sensor system, a light reflection system, a radio direction-finding system and combinations thereof, determination of a first piece of positional information relating to a position of the ultrasound probe relative to a reference system of the medical imaging apparatus based on the first items of locating data, reconstruction of the medical image data set based on the first items of imaging data, generation of the ultrasound data set based on the second items of imaging data, determination of the transformation for image registration of the ultrasound data set and the medical image data set relative to one another based on the first piece of positional information.

According to one embodiment of the invention, the following steps are provided:

generation of a fusion image based on the ultrasound data set, the medical image data set and the transformation for image registration of the ultrasound data set and the medical image data set relative to one another, outputting the fusion image.

The ultrasound data set and the medical image data set can be registered relative to one another based on the transformation for image registration. According to one embodiment of the invention, during the generation of the fusion image, the ultrasound data set and the medical image data set are registered relative to one another based on the transformation for image registration. This in particular enables the implementation of US-CT hybrid imaging.

According to one embodiment of the invention, the following steps are provided:

acquisition of second items of locating data relating to a patient via the locating system, determination of second positional information relating to a position of the patient relative to the reference system of the medical imaging apparatus based on the second items of locating data, generation of augmented-reality information based on the fusion image and based on the second positional information, wherein augmented-reality information can be used to display the fusion image superimposed on the patient, outputting the augmented-reality information.

According to one embodiment of the invention, it is provided that the medical imaging apparatus comprises a control apparatus embodied to control the medical imaging apparatus and to control the ultrasound probe, wherein the control apparatus comprises an interface, wherein control commands are output to the ultrasound probe via the interface and/or wherein the second items of imaging data are received from the ultrasound probe via the interface.

The synchronization facility for setting an operating state of a medical imaging apparatus in dependence on a temporal course of a movement of an anatomical structure and/or in dependence on a spatial distribution of an ultrasound contrast medium in the anatomical structure comprises the following components:

an ultrasound data set provisioning module embodied for the provision of an ultrasound data set relating to a temporal course of a movement of the anatomical structure and/or a spatial distribution of an ultrasound contrast medium in the anatomical structure, a trigger time determining module embodied to determine a trigger time based on the ultrasound data set, a trigger command output module embodied to output a trigger command on the onset of the trigger time, wherein the trigger command effects the setting of the operating state of the medical imaging apparatus.

According to one embodiment of the invention, it is provided that the system and/or the control apparatus comprises the synchronization facility.

Another embodiment of the present application is directed to a method for the determination of a flow parameter relating to a fluid flow and/or directed to a flow parameter determining facility. This is discussed in more detail in German application number DE 102016203809.5 filed Mar. 9, 2016, the entire contents of which are hereby incorporated herein by reference.

In at least one embodiment, the method for the determination of a flow parameter relating to a fluid flow in a segment of a vessel comprises the following steps:

provision of an ultrasound data set relating to a region to be depicted in which the vessel is located, provision of a medical image data set recorded on the basis of electromagnetic radiation and relating to the region to be depicted, determination of positional information with which the segment of the vessel can be localized in the ultrasound data set based on the medical image data set, determination of the flow parameter relating to the fluid flow in the segment of the vessel relates to based on the ultrasound data set and based on the positional information.

The medical image data set can, for example, relate to an, in particular coronary, angiography and/or be temporally correlated with the heartbeat. The vessel can in particular be a coronary vessel. During the determination of the positional information, it is in particular possible for the segment of the vessel to be identified based on the medical image data set and/or selected for a determination of the flow parameter. The determination of the flow parameter can, for example, take place within the context of a fractional flow reserve (FFR) examination. The vessel can, in particular, be a coronary vessel.

The positional information can in particular be coordinates of data points, for example image points, in the ultrasound data set and/or in the medical image data set which are assigned to the segment of the vessel. The positional information can, for example, be used as a basis for marking a position of the segment of the vessel in an ultrasound image of the ultrasound data set. This enables a non-invasive FFR examination to be performed in particular without using electromagnetic radiation and a contrast medium for the electromagnetic radiation beyond the recording of the medical image data set. Hence, the invention enables a non-invasive in-vivo fractional flow reserve examination with minimal use of X-rays and contrast medium. This also enables the sedation of the patient to be dispensed with in a catheter laboratory thus enabling the FFR examination to be performed inexpensively and with improved patient comfort.

According to one embodiment of the invention, it is provided that the ultrasound data set comprises Doppler sonography scan data. In the context of this application, the term color Doppler should be understood to mean color-coded Doppler-sonography (CCDS). Color Doppler ultrasound probes are able to measure blood flow even in relatively small vessels. However, due to the high dynamics of the heart muscle, in many cases, this is not possible or only conditionally possible with the relatively small coronary vessels. The positional information, for example, enables the position of the coronary vessels to be superimposed within the sonography image during an examination of the heart via Doppler sonography.

According to one embodiment of the invention, it is provided that a sub-region of the vessel is automatically identified based on the medical image data set and/or that the positional information is determined based on the automatically identified sub-region of the vessel.

The sub-region can, for example, be an anomaly, in particular a narrow point (stenosis), of the vessel. The segment of the vessel can in particular be a segment of the vessel located behind and/or before the narrow point of the vessel with respect to a direction of the fluid flow. It is in particular possible for a volume within which the flow parameter is determined to be automatically restricted to the automatically identified sub-region.

Skilled image registration of the medical image data set and the ultrasound data set relative to one another in connection with automatic identification (tracking) of the stenosis over the cardiac cycle enables this FFR examination to be performed almost completely automatically. When a computed tomography device is used as the medical imaging apparatus, the narrow points can, for example, examined with quantum-counting detectors and/or a material dissection for the content of certain materials, for example the calcium content.

According to one embodiment of the invention, it is provided that the medical image data set comprises a plurality of temporally successive images each relating to the region to be depicted and/or that the positional information relates to a plurality of temporally successive positions of the segment of the vessel in the ultrasound data set.

According to one embodiment of the invention, it is provided that, during the determination of the positional information, an interpolated position of the segment of the vessel in the ultrasound data set is determined and/or that the interpolated position is assigned to a time occurring between the times of two immediately temporally successive images in the plurality of temporally successive images. In particular, the movement of the coronary vessels can be interpolated between the times of the images, in particular the recordings. Hence, the position of the segment of the vessel, in particular the coronary vessel, can be localized both in the three-dimensional space and temporally over the heartbeat phases. The can in particular take placed based on the first items of locating data and/or the second items of locating data. Compute-intensive steps of the interpolation can, for example, be outsourced to a cloud.

According to one embodiment of the invention, it is provided that the plurality of temporally successive images for each heartbeat phase in a plurality of heartbeat phases comprises at least one image assigned to the respective heartbeat phase and/or that the plurality of temporally successive positions of the segment for each heartbeat phase in the plurality of heartbeat phases comprises at least one position assigned to the respective heartbeat phase. The heartbeat phases can in particular be understood to mean different heartbeat phases of a cardiac cycle. It, for example, possible for a plurality of angiograms to be performed in different heartbeat phases and for the movement of coronary vessels to be interpolated between the times of the images, in particular the recordings.

According to one embodiment of the invention, it is provided that the vessel is a blood vessel is and/or wherein the fluid flow is a blood flow. The fluid can in particular be blood and/or a blood/contrast-medium mixture.

According to one embodiment of the invention, it is provided that the flow parameter is selected from the parameter group consisting of a speed, a direction, a density, a pressure and an energy of the fluid flow. The density can in particular be a particle density and/or a mass density.

According to one embodiment of the invention, the following steps are provided:
acquisition of first items of imaging data of the region to be depicted via a medical imaging apparatus based on electromagnetic radiation,
reconstruction of the medical image data set based on the first items of imaging data.

The provision of the medical image data set can, for example, include the reconstruction of the medical image data set based on the first items of imaging data and/or the acquisition of the first items of imaging data via the medical imaging apparatus. Alternatively or additionally thereto, the provision of the medical image data set can include loading the medical image data set from an image database. According to one embodiment of the invention, the following steps are provided:
acquisition of second items of imaging data via an ultrasound probe,
generation of the ultrasound data set based on the second items of imaging data.

The provision of the ultrasound data set can, for example, include the generation of the ultrasound data set based on the second items of imaging data and/or the acquisition of the second items of imaging data via the ultrasound probe. Alternatively or additionally thereto, the provision of the ultrasound data set can include loading the ultrasound data set from an image database.

According to one embodiment of the invention, the following steps are provided:
determination of a transformation for image registration of the ultrasound data set and the medical image data set,
registration of the ultrasound data set and the medical image data set relative to one another based on the transformation for image registration.

The transformation for image registration can in particular be determined by way of a method described in this application for the determination of a transformation of an ultrasound data set and a medical image data set recorded with electromagnetic radiation relative to one another.

According to one embodiment of the invention one or more of following components is/are provided:
an ultrasound data set provisioning module embodied for the provision of an ultrasound data set relating to a region to be depicted in which the vessel is located,
an image data set provisioning module embodied for the provision of a medical image data set recorded on the basis of electromagnetic radiation and relating to the region to be depicted,
a positional information determining module embodied to determine positional information with which the segment of the vessel in the ultrasound data set can be localized and/or relating to a position of the segment of the vessel based on the medical image data set,
a flow parameter determining module embodied for the determination of the flow parameter relating to the fluid flow through the segment of the vessel based on the ultrasound data set and based on the positional information.

The flow parameter determining facility for the determination of a flow parameter relating to a fluid flow through a segment of a vessel comprises the following components:
an ultrasound data set provisioning module,
an image data set provisioning module,
a positional information determining module,
a flow parameter determining module.

In particular, the positional information determining module can be embodied to select a sub-region of the vessel based on the medical image data set and/or to determine the positional information based on the selected sub-region of the vessel.

According to one embodiment of the invention, it is provided that the flow parameter determining facility is embodied to carry out a method for the determination of a flow parameter according to one or more of the embodiments described in this application.

According to one embodiment of the invention, it is provided that the system comprises the following components:
a medical imaging apparatus embodied for the acquisition of first items of imaging data based on electromagnetic radiation,
the flow parameter determining facility.

According to one embodiment of the invention, it is provided that the system is embodied to carry out a method according to one or more of the embodiments described in this application. The system is in particular embodied to carry out a given step when the system comprises a component embodied to carry out the given step.

One embodiment of the invention provides that the control apparatus is formed by a computer and/or that one or more components of the control apparatus are formed at least partially by a computer. The computer can, for example, comprise a memory facility and/or a processor system. The processor system can, for example, comprise a microprocessor and/or a plurality of interacting microprocessors. One embodiment of the invention provides that the control apparatus and/or one or more components of the control apparatus is or are implemented at least partially in the form of software on a processor system.

One embodiment of the invention provides that the control apparatus and/or one or more components of the control apparatus is or are implemented at least partially in the form of hardware. The hardware can, for example, be an FPGA system (Field-programmable gate array), an ASIC system (application-specific integrated circuit), a microcontroller system, a processor system and combinations thereof. The hardware can, for example, interact with software and/or be configured by way of software. One embodiment of the invention provides that the control apparatus and/or one or more components of the control apparatus is or are at least partially formed by a cloud via cloud computing. The cloud can in particular comprise a network of memory regions that are spatially separated from one another and processor systems that are spatially separated from one another. The control apparatus can comprise a first cloud interface for the data transfer from the cloud and/or to the cloud.

Data transfer between components of the control apparatus can, for example, in each case take place via a suitable data transfer interface. One embodiment of the invention provides that data transfer interfaces for transferring data to and/or from components of the control apparatus are implemented at least partially in the form of software and/or at least partially in the form of hardware. In particular, the interfaces can comprises means for accessing suitable memory regions in which data can be suitably buffered, retrieved and updated.

In particular with an extensively software-based implementation of the control apparatus, a computer can be embodied by way of software such that the computer can carry out the steps of a method according to at least one embodiment of the invention. Hence, the object is in each case achieved by the computer program according to at least one embodiment of the invention, the computer-readable medium according to at least one embodiment of the invention and the computer program product according to at least one embodiment of the invention.

The computer program according to at least one embodiment of the invention can be loaded into a memory facility of a computer. The computer program carries out the steps of a method according to at least one embodiment of the invention when the computer program is executed on the computer. A computer program according to at least one embodiment of the invention is stored on the computer-readable medium according to at least one embodiment of the invention. In particular, the computer-readable medium can be embodied to transport the computer program and/or to store the computer program.

According to one embodiment of the invention, the computer-readable medium is a memory stick, a hard disk or some other kind of a data medium that can, for example, be transportable or permanently installed. The computer program according to at least one embodiment of the invention product comprises a computer program according to the invention and/or a computer-readable medium according to at least one embodiment of the invention. In addition to the computer program and/or the computer-readable medium, the computer program product can include additional software components, for example documentation, and/or additional hardware components, for example a hardware key (dongle etc.) for using the software.

One embodiment of the invention provides that the described method and/or one or more steps of the described method is or are in each case carried out automatically and/or fully automatically. In particular, a sub-region of the vessel can be identified automatically and/or fully automatically based on the medical image data set.

In the context of the present application, "automatically" means that the respective step is carried out independently by way of software and/or by way of hardware and/or that the respective step substantially does not require any interaction with a user. In particular, substantially no interaction is required if the user only accepts or rejects one or more automatically generated suggestions. In the context of the present application, "fully automatically" means that no interaction at all with a user is needed to carry out the respective step. Regardless of whether one or more steps are carried out "automatically" or "fully automatically", the method according to at least one embodiment of the invention can be a component of an operating sequence that additionally requires interaction with a user. The interaction of the user can, for example, reside in the fact that the user compiles or selects an examination protocol and/or an examination plan and/or a clinical issue manually, for example from a menu presented via a screen.

In the context of at least one embodiment of the invention, features described with regard to different embodiments of the invention and/or different claim categories (apparatus, method etc.) can be combined to form further embodiments of the invention. In other words, the substantive claims can also be developed with the features described or claimed in connection with a method. Functional features of a method according to at least one embodiment of the invention can also be carried out by correspondingly embodied substantive components. In addition to the embodiments of the invention expressly described in this application, multiple further embodiments of the invention are conceivable which the person skilled in the art will be able to arrive at without leaving the scope of the invention as described in the claims.

The use of indefinite article "a" or "an" does not preclude the possibility of the features in question also being present on a multiple basis. The use of the term "comprise" does not preclude the possibility of the terms being linked by the term "comprise" being identical. For example the medical imaging apparatus comprises the medical imaging apparatus. The use of the term "unit" does not preclude the possibility of the subject matter to which the term "unit" relates comprising a plurality of components that are spatially separated from one another. In the context of the present application, the use of ordinal numbers (first, second, third etc.) in the description of features is primarily for better distinction of features described using ordinal numbers. The absence of a feature described by a combination of a given ordinal number and of a term does not preclude the possibility of a feature being present that is also described by a combination of an ordinal number following the given ordinal number and the term.

In the context of the present application, the expression "based on" can in particular be understand as meaning "using". In particular, wording according to which a first feature is created (alternatively: determined, identified etc.) based on a second feature does not preclude the possibility of the first feature being created (alternatively: determined, identified etc.) based on a third feature.

FIG. 1 shows a schematic representation of the system 1 according to a first embodiment of the invention. The system 1 comprises the medical imaging apparatus 2, the control apparatus 30, the ultrasound probe TP, the injection apparatus IU, the location system LS and the augmented-reality apparatus AD.

Without restricting the general concept of the invention, a computed tomography device is shown by way of example for the medical imaging apparatus 2. The medical imaging apparatus 2 comprises the gantry 20, the tunnel-shaped opening 9, the patient support apparatus 10 and the control apparatus 30. The gantry 20 comprises the stationary carrying frame 21 and the rotor 24. The rotor 24 is arranged rotatably on the stationary carrying frame 21 about an axis of rotation relative to the stationary carrying frame 21 by way of a rotary bearing apparatus. The patient 13 can be introduced into the tunnel-shaped opening 9. The acquisition region 4 is located in the tunnel-shaped opening 9. In the acquisition region 4, a region to be depicted of the patient 13 can be positioned such that the radiation 27 can travel from the radiation source 26 to the region to be depicted and, following interaction with the region to be depicted, travel to the radiation detector 28. The patient support apparatus 10 comprises the supporting table 11 and the transfer plate 12 for supporting the patient 13. The transfer plate 12 is arranged movably on the supporting table 11 relative to the supporting table 11 such that the transfer plate 12 can be introduced into the acquisition region 4 in a longitudinal direction of the transfer plate 12.

The medical imaging apparatus 2 is embodied for the acquisition A1 of first items of imaging data based on electromagnetic radiation 27. The medical imaging apparatus 2 comprises an imaging data acquisition unit. The imaging acquisition unit is a projection data acquisition unit with the radiation source 26, for example an X-ray source, and the detector 28, for example an X-ray detector, in particular an energy-resolving X-ray detector. The radiation source 26 is arranged on the rotor 24 and embodied for the emission of radiation 27, for example X-rays, with radiation quanta 27. The detector 28 is arranged on the rotor 24 and embodied to detect the radiation quanta 27. The radiation quanta 27 can travel from the radiation source 26 to the region to be depicted of the patient 13 and, following interaction with the region to be depicted, arrive at the detector 28. In this way, the imaging data acquisition unit is able to acquire first items of imaging data of the region to be depicted in the form of projection data.

The control apparatus 30 is embodied to receive the first items of imaging data acquired from the imaging data acquisition unit. The control apparatus 30 is embodied to control the medical imaging apparatus 2. The control apparatus 30 comprises the image reconstruction facility 34. The image reconstruction facility 34 can reconstruct a medical image data set based on the first items of imaging data. The control apparatus 30 is further embodied to control the ultrasound probe TP. The control apparatus 30 comprises the interface CI which is embodied to output control commands to control the ultrasound probe TP to the ultrasound probe TP. The ultrasound probe TP can be connected to the control apparatus 30 via the interface OI.

The control apparatus 30 comprises the synchronization facility 35 and the flow parameter determining facility 36. The control apparatus 30 comprises a computer 30 and a tablet computer TC. The computer 30 comprises a memory facility 31 and a processor system. A computer program, which is stored on the computer-readable medium 32, can be loaded into the memory facility 31 of the computer 30. The computer 30 is embodied to execute the computer program. The medical imaging apparatus 2 comprises an input apparatus 38 and an output apparatus 39 each of which are connected to the control apparatus 30. The input apparatus 38 is embodied to input control information, for example image reconstruction parameters and/or examination parameters. The output apparatus 39 is in particular embodied to output control information, images and/or sounds.

The augmented-reality apparatus AD is connected to the control apparatus 30 and is embodied both to input control information and to display augmented-reality information, the fusion image, the medical image data set, the ultrasound data set and/or further information. The augmented-reality apparatus AD can be used to display the augmented-reality information in a field of view of the user U1. The location system LS comprises the camera system KS and the optical sensor system OS.

Figure 2:
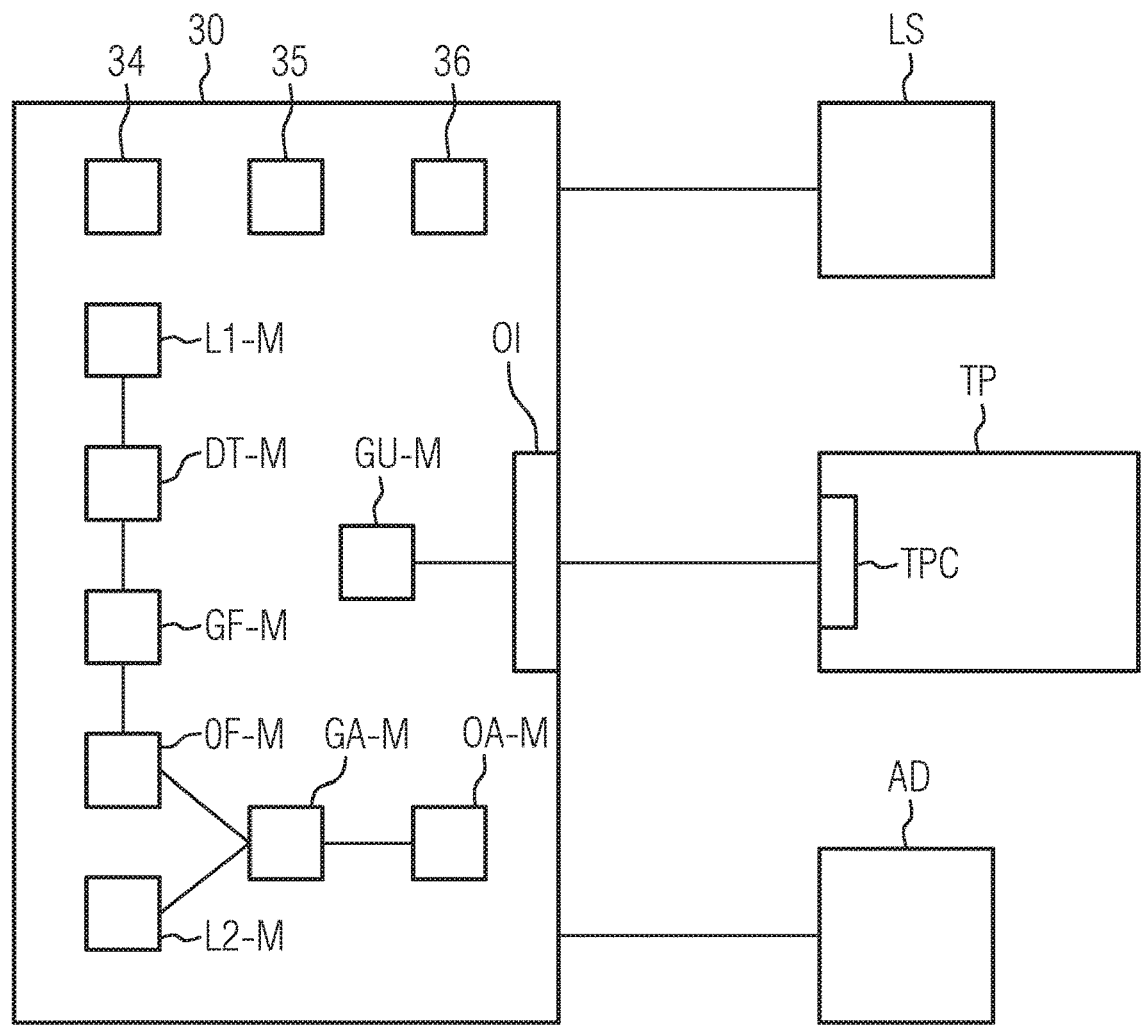

FIG. 2 shows a schematic representation of the control apparatus 30. The control apparatus 30 comprises the ultrasound data set generation module GU-M, the first positional information determining module L1-M, the transformation determining module DT-M, the fusion image generating module GF-M, the fusion image output module OF-M, the second positional information determining module L2-M, the augmented-reality information generating module GA-M and the augmented-reality information output module GA-M. The control apparatus 30 is connected to the augmented-reality apparatus AD and the location system LS. The ultrasound probe TP is connected to the control apparatus 30 via the interface OI. The ultrasound probe TP comprises a data transmission module TPC embodied to receive the control commands from the interface OI and to output the second items of imaging data to the interface OI. The data transmission module TPC comprises a data transmission connector embodied for direct data transmission of the control commands from the interface OI and/or for direct data transmission of the second items of imaging data to the interface OI.

Figure 3:
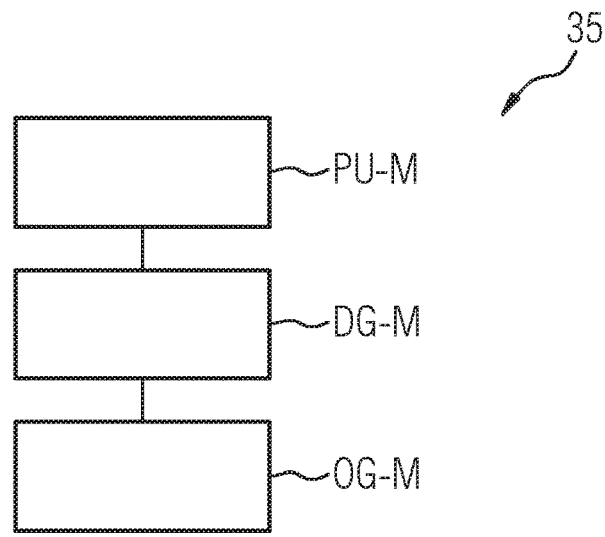

FIG. 3 shows a schematic representation of the synchronization facility 35 according to a second embodiment of the invention. The synchronization facility 35 comprises the ultrasound data set provisioning module PU-M, the trigger time determining module DG-M and the trigger command output module OG-M.

FIG. 4 shows a schematic representation of the flow parameter determining facility 36. The flow parameter determining facility 36 comprises the ultrasound data set provisioning module PU-M, the image data set provisioning module PI-M, the positional information determining module DP-M and the flow parameter determining module DW-M.

FIG. 5 shows a flow diagram of a method for the determination of a transformation for image registration of an ultrasound data set and a medical image data set recorded with electromagnetic radiation 27 relative to one another according to a third embodiment of the invention. The method shown in FIG. 5 comprises the following steps:

acquisition A1 of first items of imaging data via a medical imaging apparatus 2 based on electromagnetic radiation 27, acquisition A2 of second items of imaging data via an ultrasound probe TP, acquisition S1 of first items of locating data relating to the ultrasound probe TP via a locating system LS selected from the location system group including of a camera system KS, an optical sensor system OS, a light reflection system, a radio direction-finding system and combinations thereof, determination L1 of a first piece of positional information relating to a position of the ultrasound probe TP relative to a reference system of the medical imaging apparatus 2, based on the first items of locating data, reconstruction RI of the medical image data set based on the first items of imaging data, generation GU of the ultrasound data set based on the second items of imaging data, and determination DT of the transformation for image registration.

The method shown in FIG. 5 further comprises the following steps:

generation GF of a fusion image based on the ultrasound data set, the medical image data set and the transformation for image registration of the ultrasound data set and the medical image data set relative to one another, outputting OF the fusion image, acquisition S2 of second items of locating data relating to a patient 13, via the locating system LS, determination L2 of second positional information relating to a position of the patient 13 relative to the reference system of the medical imaging apparatus 2 based on the second items of locating data, generation GA of augmented-reality information based on the fusion image and based on the second positional information, wherein augmented-reality information can be used to display the fusion image superimposed on the patient 13, outputting OA the augmented-reality information.

Figure 6:
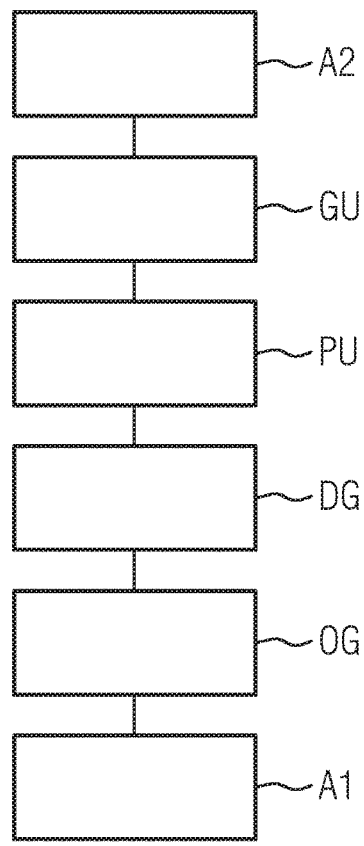

FIG. 6 shows a flow diagram of a method for setting an operating state of the medical imaging apparatus 2 according to a fourth embodiment of the invention. The method shown in FIG. 6 comprises the following steps:

acquisition A2 of second items of imaging data of a region to be depicted in which the anatomical structure is located via an ultrasound probe TP, generation GU of the ultrasound data set based on the second items of imaging data, provision PU of an ultrasound data set relating to a temporal course of a movement of the anatomical structure and/or a spatial distribution of an ultrasound contrast medium in the anatomical structure, determination DG of a trigger time based on the ultrasound data set, outputting OG a trigger command on the onset of the trigger time, wherein the trigger command effects the setting of the operating state of the medical imaging apparatus 2.

acquisition A1 of the first items of imaging data via the medical imaging apparatus 2 based on the electromagnetic radiation 27.

Figure 7:
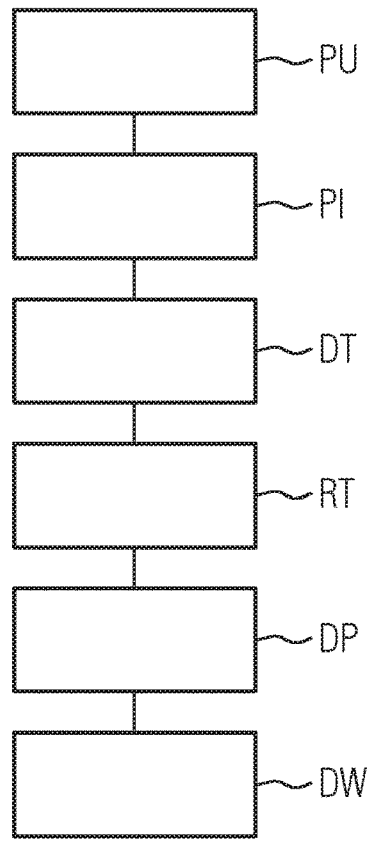

FIG. 7 shows a flow diagram of a method for the determination of a flow parameter relating to a fluid flow in a segment VS1, VS2 of a vessel V. The method shown in FIG. 7 comprises the following steps:

provision PU of an ultrasound data set relating to a region to be depicted in which the vessel V is located, provision PI of a medical image data set recorded based on electromagnetic radiation 27 and relating to the region to be depicted, determination DT of a transformation for image registration of the ultrasound data set and the medical image data set, registration RT of the ultrasound data set and the medical image data set relative to one another based on the transformation for image registration, determination DP of positional information with which the segment VS1, VS2 of the vessel V can be localized in the ultrasound data set based on the medical image data set, determination DW of the flow parameter relating to the fluid flow in the segment VS1, VS2 of the vessel V based on the ultrasound data set and based on the positional information.

The flow parameter determining facility 36 is embodied to carry out a method for the determination of a flow parameter, relating to a fluid flow in a segment VS1, VS2 of a vessel V according to one of the embodiments described in this application. In particular, the method shown in FIG. 7 can be used for the determination of a flow parameter via the flow parameter determining facility 36.

Figure 8:
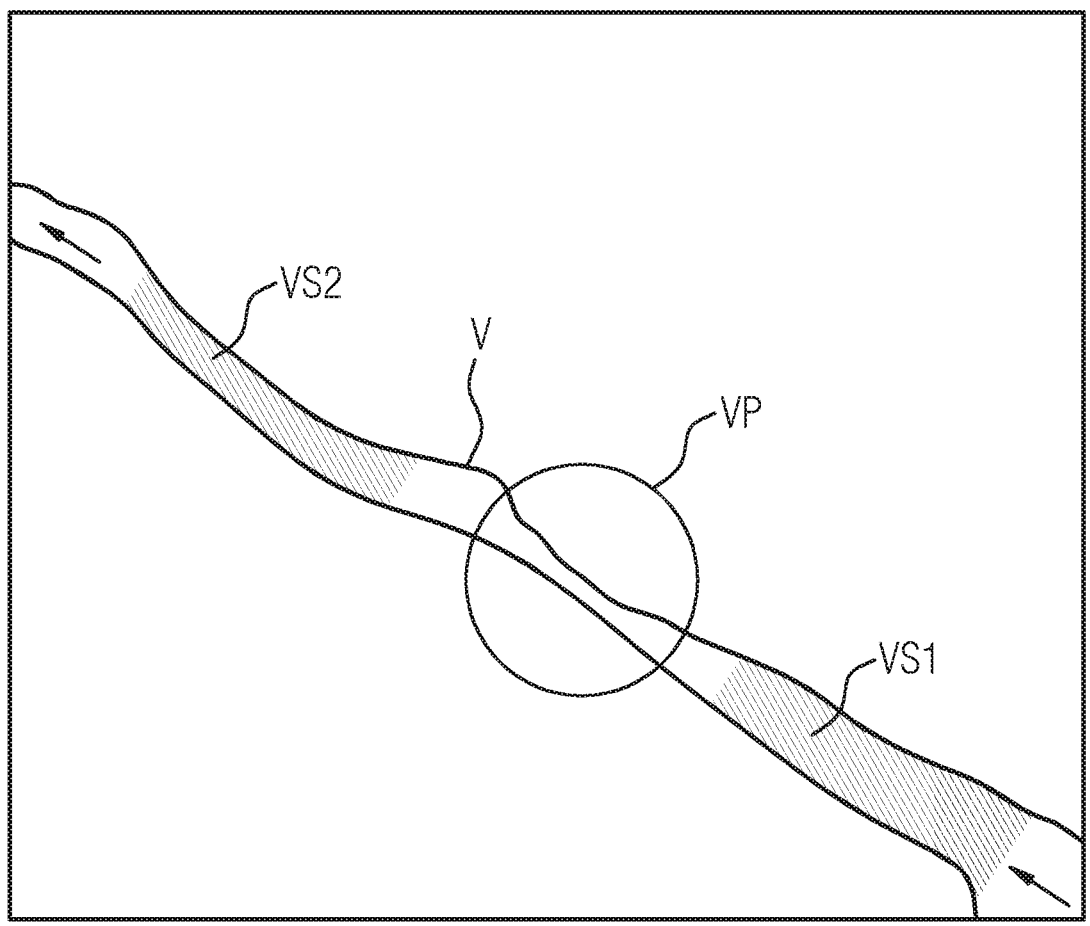

FIG. 8 shows a schematic representation of the vessel V. The sub-region VP of the vessel V is a narrow point (stenosis). The direction of the fluid flow is indicated by arrows. The segment VS1 of the vessel V is located with regard to the direction of the fluid flow before the narrow point VP. The segment VS2 of the vessel V is located with regard to the direction of the fluid flow after the narrow point VP.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A system, comprising:
a medical imaging apparatus embodied to acquire first items of imaging data based on electromagnetic radiation; and
a control apparatus embodied to control the medical imaging apparatus and to control an ultrasound probe, the control apparatus including an interface embodied to output control commands to the ultrasound probe, wherein the ultrasound probe is connectable to the control apparatus via the interface, wherein at least one of the system and the control apparatus includes a synchronization facility comprising:
an ultrasound data set provisioning module embodied to provision an ultrasound data set relating to at least one of a temporal course of a movement of the anatomical structure and a spatial distribution of an ultrasound contrast medium in the anatomical structure;
a trigger time determining module embodied to determine a trigger time based on the ultrasound data set; and
a trigger command output module embodied to output a trigger command on the onset of the trigger time, wherein the trigger command is configured to affect the setting of the operating state of the medical imaging apparatus.

2. The system of claim 1, further comprising the ultrasound probe.

3. The system of claim 1, wherein the ultrasound probe is embodied to acquire second items of imaging data.

4. The system of claim 1, wherein the interface is embodied to receive the second items of imaging data from the ultrasound probe.

5. The system of claim 1, wherein the control apparatus further includes an ultrasound data set generation module embodied to generate an ultrasound data set based on the second items of imaging data.

6. The system of claim 1, wherein the ultrasound probe is connected to the control apparatus via the interface.

7. The system of claim 1, wherein the interface is at least one of an open and universal interface.

8. The system of claim 1, wherein the interface is selected from the interface group consisting of a USB interface, a FireWire interface, a Bluetooth interface and combinations thereof.

9. The system of claim 1, wherein the control apparatus further includes a mobile control unit, and wherein the mobile control unit comprises the interface.

10. The system of claim 9, wherein the mobile control unit is a tablet computer.

11. The system of claim 9, wherein the medical imaging apparatus comprises at least one of a gantry and a patient support apparatus, and wherein the mobile control unit is at least one of arranged and arrangeable on the at least one of the gantry and the patient support apparatus.

12. The system of claim 1, further comprising:
an injection apparatus, embodied to apply a contrast medium for the acquisition of the first items of imaging data based on at least one of the electromagnetic radiation and an ultrasound contrast medium.

13. A system, comprising:
a medical imaging apparatus embodied to acquire first items of imaging data based on electromagnetic radiation;
a control apparatus embodied to control the medical imaging apparatus and to control an ultrasound probe, the control apparatus including an interface embodied to output control commands to the ultrasound probe, wherein the ultrasound probe is connectable to the control apparatus via the interface; and
a location system selected from a location system group including a camera system, an optical sensor system, a light reflection system, a radio direction-finding system and combinations thereof, wherein the location system is embodied to acquire at least one of first items of locating data relating to the ultrasound probe and second items of locating data relating to a patient, wherein the control apparatus further comprises:
a first positional information determining module embodied to determine a first piece of positional information relating to a position of the ultrasound probe relative to a reference system of the medical imaging apparatus based on the first items of locating data,
a transformation determining module embodied to determine a transformation for image registration of an ultrasound data set and a medical image data set based on the first piece of positional information,
a fusion image generating module embodied to generate a fusion image based on the ultrasound data set, the medical image and the transformation for image registration of the ultrasound data set and the medical image data set,
a fusion image output module embodied to output the fusion image,
a second positional information determining module embodied to determine second positional information relating to a position of the patient relative to the reference system of the medical imaging apparatus based on the second items of locating data,
an augmented-reality information generating module embodied to generate augmented-reality information based on the fusion image and based on the second positional information, wherein augmented-reality information is useable to display the fusion image superimposed on the patient, and an augmented-reality information output module embodied to output the augmented-reality information.

14. A method for setting an operating state of a medical imaging apparatus embodied to acquire first items of imaging data based on electromagnetic radiation in dependence on at least one of a temporal course of a movement of an anatomical structure and a spatial distribution of an ultrasound contrast medium in the anatomical structure, the method comprising:
provisioning an ultrasound data set relating to a temporal course of a movement of at least one of the anatomical structure and a spatial distribution of an ultrasound contrast medium in the anatomical structure;
determining a trigger time based on the ultrasound data set; and
outputting a trigger command on the onset of the trigger time, wherein the trigger command affects the setting of the operating state of the medical imaging apparatus.

15. The method of claim 14, further comprising:
acquiring second items of imaging data of a region to be depicted in which the anatomical structure is located via an ultrasound probe; and
generating the ultrasound data set based on the second items of imaging data.

16. The method of claim 14, further comprising:
acquiring the first items of imaging data via the medical imaging apparatus based on the electromagnetic radiation.

17. The method of claim 14,
wherein the medical imaging apparatus comprises a control apparatus embodied to control the medical imaging apparatus and to control the ultrasound probe,
wherein the control apparatus comprises an interface, and wherein at least one of
control commands are output to the ultrasound probe via the interface, and
the second items of imaging data are received from the ultrasound probe via the interface.

18. A synchronization facility for setting an operating state of a medical imaging apparatus in dependence on at least one of a temporal course of a movement of an anatomical structure and a spatial distribution of an ultrasound contrast medium in the anatomical structure, the synchronization facility comprising:
an ultrasound data set provisioning module embodied to provision an ultrasound data set relating to at least one of the temporal course of a movement of the anatomical structure and the spatial distribution of an ultrasound contrast medium in the anatomical structure;
a trigger time determining module embodied to determine a trigger time based on the ultrasound data set; and
a trigger command output module embodied to output a trigger command on the onset of the trigger time, wherein the trigger command is configured to affect the setting of the operating state of the medical imaging apparatus.

19. The system of claim 13 embodied to carry out a method comprising:
provisioning an ultrasound data set relating to a temporal course of a movement of at least one of the anatomical structure and a spatial distribution of an ultrasound contrast medium in the anatomical structure;
determining a trigger time based on the ultrasound data set; and outputting a trigger command on the onset of the trigger time, wherein the trigger command affects the setting of the operating state of the medical imaging apparatus.

20. The system of claim 2, wherein the ultrasound probe is embodied to acquire second items of imaging data.

21. The system of claim 2, wherein the interface is embodied to receive the second items of imaging data from the ultrasound probe.

22. The system of claim 2, wherein the control apparatus further includes an ultrasound data set generation module embodied to generate an ultrasound data set based on the second items of imaging data.

23. The system of claim 2, wherein the control apparatus further comprises a mobile control unit, and wherein the mobile control unit comprises the interface.

24. The system of claim 23, wherein the medical imaging apparatus comprises at least one of a gantry and a patient support apparatus, and wherein the mobile control unit is at least one of arranged and arrangeable on the at least one of the gantry and the patient support apparatus.

25. The system of claim 2, further comprising:
an injection apparatus, embodied to apply a contrast medium for the acquisition of the first items of imaging data based on at least one of the electromagnetic radiation and an ultrasound contrast medium.

26. The method of claim 15, further comprising:
acquiring the first items of imaging data via the medical imaging apparatus based on the electromagnetic radiation.

27. A non-transitory computer readable medium including program code for carrying out the method of claim 14 when the program code is run in a computer.

* * * * *